(12) United States Patent
Kim et al.

(10) Patent No.: US 12,570,595 B2
(45) Date of Patent: Mar. 10, 2026

(54) PROCESS FOR PRODUCING ACRYLIC ACID

(71) Applicant: LG CHEM, LTD., Seoul (KR)

(72) Inventors: Hyebin Kim, Daejeon (KR); Mi Kyung Kim, Daejeon (KR); Eunkyo Kim, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 714 days.

(21) Appl. No.: 17/921,693

(22) PCT Filed: Oct. 27, 2021

(86) PCT No.: PCT/KR2021/015165
§ 371 (c)(1),
(2) Date: Oct. 27, 2022

(87) PCT Pub. No.: WO2022/119123
PCT Pub. Date: Jun. 9, 2022

(65) Prior Publication Data
US 2023/0174453 A1    Jun. 8, 2023

(30) Foreign Application Priority Data
Dec. 3, 2020    (KR) ........................ 10-2020-0167638

(51) Int. Cl.
*C07C 51/47*        (2006.01)
*C07C 51/44*        (2006.01)

(52) U.S. Cl.
CPC .............. *C07C 51/47* (2013.01); *C07C 51/44* (2013.01)

(58) Field of Classification Search
CPC ................................ C07C 51/47; C07C 51/44
See application file for complete search history.

(56) References Cited

U.S. PATENT DOCUMENTS

| | | |
|---|---|---|
| 6,639,106 B1 | 10/2003 | Elder et al. |
| 8,246,790 B2 | 8/2012 | Baek et al. |
| 8,609,893 B2 | 12/2013 | Devaux et al. |
| 9,662,646 B2 | 5/2017 | You et al. |
| 10,308,582 B2 | 6/2019 | Binder et al. |
| 10,350,539 B2 | 7/2019 | Song et al. |

(Continued)

FOREIGN PATENT DOCUMENTS

| | | |
|---|---|---|
| CN | 1282727 | 2/2001 |
| CN | 101255109 | 9/2008 |

(Continued)

*Primary Examiner* — Amy C Bonaparte
*Assistant Examiner* — Derek Rhoades
(74) *Attorney, Agent, or Firm* — Bryan Cave Leighton Paisner LLP

(57) ABSTRACT

Provided is a process for producing acrylic acid, wherein the process comprises a first step and a second step in which a first absorbent is added to a reaction product of a bio-material and cooled to separate a first low-boiling-point material including acetaldehyde (ACHO) and a first high-boiling-point material including acrylic acid (AA). The process is capable of producing high-purity acrylic acid at high yield, and acetaldehyde is produced as by-product along with the reaction product of the bio-material. The process includes separating the acetaldehyde produced as by-product into a high-purity product at high yield.

10 Claims, 2 Drawing Sheets

(56)  References Cited

U.S. PATENT DOCUMENTS

| | | | |
|---|---|---|---|
| 10,919,834 B2 | 2/2021 | Kase et al. | |
| 10,961,179 B2 | 3/2021 | Fauconet et al. | |
| 2007/0173667 A1 | 7/2007 | Sakai et al. | |
| 2010/0113822 A1 | 5/2010 | Craciun et al. | |
| 2012/0302797 A1* | 11/2012 | Devaux et al. | C07C 45/00 |
| | | | 568/486 |
| 2013/0273384 A1 | 10/2013 | Godlewski et al. | |
| 2015/0299084 A1 | 10/2015 | Shimizu et al. | |

FOREIGN PATENT DOCUMENTS

| | | |
|---|---|---|
| CN | 104884421 | 9/2015 |
| JP | 6772376 | 10/2010 |
| JP | 2014189510 | 10/2014 |
| JP | 2015-518481 | 7/2015 |
| JP | 6574838 | 9/2019 |
| KR | 10-0584677 | 5/2006 |
| KR | 10-2009-0041355 | 4/2009 |
| KR | 20150096745 | 8/2015 |
| KR | 10-2016-0018699 | 2/2016 |
| KR | 10-1815440 | 1/2018 |
| KR | 10-2018-0064432 | 6/2018 |
| KR | 10-2080287 | 2/2020 |
| WO | 2005-095320 | 10/2005 |

* cited by examiner

【FIG. 1】
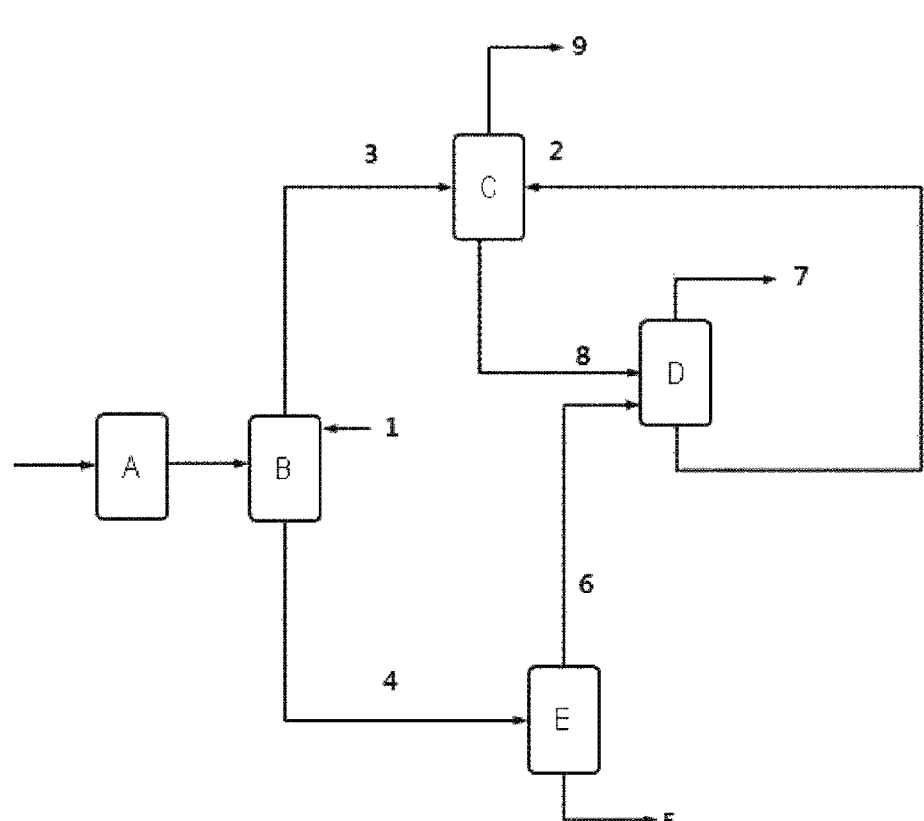

【FIG. 2】
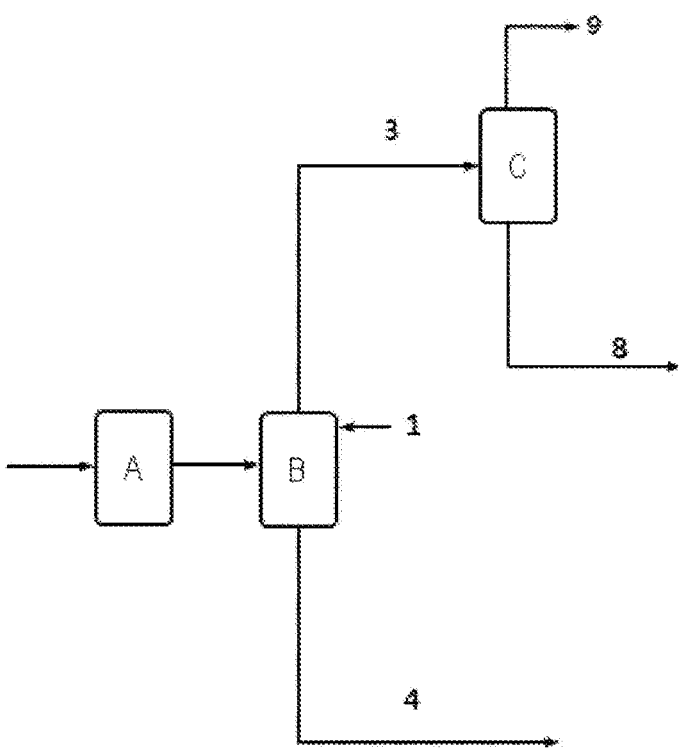
【FIG. 3】
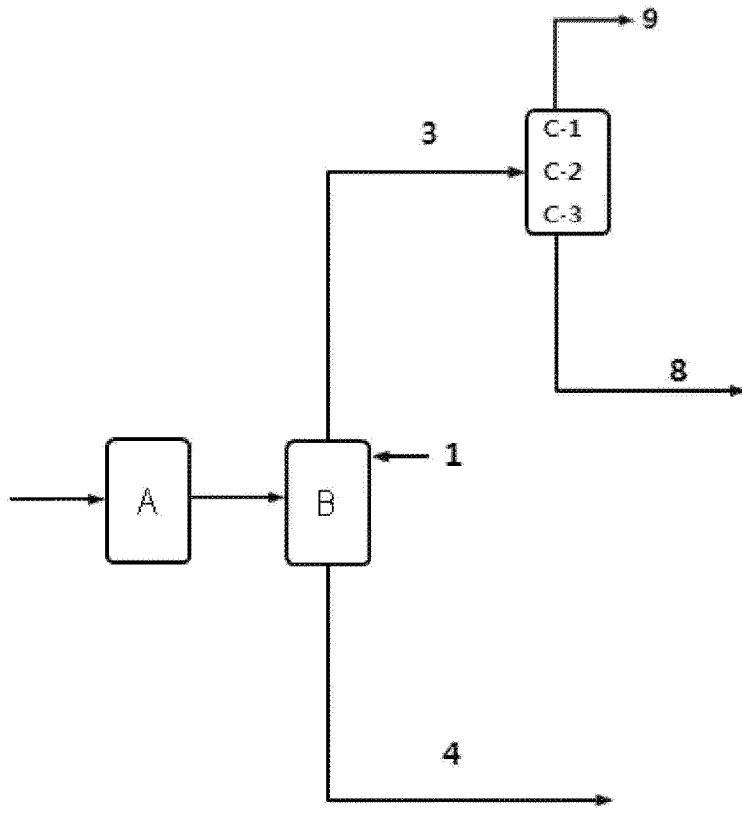

PROCESS FOR PRODUCING ACRYLIC ACID

CROSS-REFERENCE TO RELATED APPLICATION(S)

This application is a National Stage Application of International Application No. PCT/KR2021/015165 filed on Oct. 27, 2021, which claims priority to and the benefits of Korean Patent Application No. 10-2020-0167638, filed with the Korean Intellectual Property Office on Dec. 3, 2020, the entire contents of which are incorporated herein by reference.

TECHNICAL FIELD

The present application relates to a process for producing acrylic acid.

BACKGROUND

Acrylic acid has been generally produced through an oxidative dehydrogenation reaction of propylene, and demands on acrylic acid have increased as a raw material of super absorbent polymers, paints, adhesives and the like. Particularly, super absorbent polymers are used as hygiene products such as diapers.

So far, a considerable number of chemical products have been produced using raw materials derived from fossil raw materials such as coal or petroleum. However, using recyclable bio-derived resources as a carbon source has recently received attention as a substitute for existing fossil raw materials in terms of preventing global warming and protecting the environment. For example, development of methods using biomass resources including starch-based biomass such as corn or wheat, carbohydrate-based biomass such as sugar cane, cellulose-based biomass such as residue of rapeseed or rice straw, and the like as a raw material has been attempted.

In order words, studies on breaking from existing petrochemical-based manufacturing processes and producing chemical products based on environmental-friendly raw materials to obtain excellent properties in terms of environmental protection while obtaining sustainability are recently in progress.

One type of reactions producing other chemical products from lactic acid can include a gas-phase reaction in which a raw material including lactic acid is evaporated and brought into contact with a catalyst in a gaseous state to obtain a product. For example, as a technology of producing acrylic acid using lactic acid, a gas-phase dehydration reaction using a solid catalyst is known, and the dehydration reaction of lactic acid is mainly studied as a gas-phase reaction.

Lactic acid is a substance that polymerizes as an esterification reaction that occurs in a liquid phase without a catalyst in the absence of water, and reacts as a lactic acid oligomer as lactic acid is concentrated and a concentration thereof increases. Dehydration occurs as lactic acid is oligomerized, and an oligomerization reaction of lactic acid occurs as the lactic acid is concentrated without water. When the lactic acid oligomer is introduced to a reactor for producing acrylic acid, fouling occurs in the reactor and the reaction yield decreases, and therefore, studies on a method to decrease the content of lactic acid oligomer for producing acrylic acid is in progress.

In addition to such a problem, economic feasibility needs to be enhanced in developing the process since reactions of bio-raw materials show low acrylic acid selectivity compared to existing petrochemical reactions such as an oxidation reaction of propylene.

Particularly, when producing bio-raw material-based acrylic acid, by-products such as carbon monoxide, carbon dioxide and acetaldehyde, which are by-products having a low boiling point, are produced together with acrylic acid production, lowering acrylic acid selectivity, and accordingly, studies on a process to smoothly separate by-products such as low boiling point by-products and acrylic acid and increase purity of the low boiling point by-products themselves for commercialization when producing bio-raw material-based acrylic acid are in progress.

Prior Art Documents (Patent Document 1) International Patent Publication No. WO 2005/095320 A1

BRIEF DESCRIPTION

Technical Problem

The present application is directed to providing a process for producing acrylic acid.

Technical Solution

One embodiment of the present application provides a process for producing acrylic acid, the process including a step 1 of separating a first low-boiling-point material including acetaldehyde (ACHO) and a first high-boiling-point material including acrylic acid (AA) by adding a first absorbent to a reaction product of a bio-raw material and cooling the result; a step 2 of separating a second low-boiling-point material including acetaldehyde (ACHO) and a second high-boiling-point material including acrylic acid (AA) by distilling the first high-boiling-point material including acrylic acid (AA); a step 3 of separating a first incompressible material and a third low-boiling-point material including acetaldehyde (ACHO) by adding a second absorbent to the first low-boiling-point material including acetaldehyde (ACHO) and cooling the result; and a step 4 of producing acrylic acid by purifying the second high-boiling-point material including acrylic acid (AA).

Advantageous Effects

A process for producing acrylic acid according to one embodiment of the present application includes a step 1 of separating a first low-boiling-point material including acetaldehyde (ACHO) and a first high-boiling-point material including acrylic acid (AA) by adding a first absorbent to a reaction product of a bio-raw material and cooling the result, and a step 2 of separating a second low-boiling-point material including acetaldehyde (ACHO) and a second high-boiling-point material including acrylic acid (AA), and accordingly, final acrylic acid can be produced in high purity and high yield.

Particularly, acetaldehyde is produced as a by-product in the reaction product of the bio-raw material since a dehydration reaction of lactic acid occurs at a high temperature (330° C. to 400° C.), and by the process for producing acrylic acid according to the disclosure of the present application including a step 3 in the process, acetaldehyde produced as a by-product can be commercialized as a high purity and high yield product while producing high purity and high yield acrylic acid as above, which enhances economic feasibility of the bioprocess since both acrylic acid and acetaldehyde can be obtained.

DESCRIPTION OF THE DRAWINGS

FIG. 1 is a schematic diagram illustrating a process for producing acrylic acid according to one embodiment of the present application.

FIG. 2 is a schematic diagram illustrating a process for producing acrylic acid according to Comparative Example 1 of the present application.

FIG. 3 is a schematic diagram illustrating a process for producing acrylic acid according to Comparative Example 1 of the present application.

REFERENCE NUMERALS

A: Reaction Product of Bio-Raw Material
B: Cooling Tower
C: Absorption Tower
C-1, C-2, C-3: Additional Cooling Process
D: Separation Tower
E: Distillation Tower
1: First Absorbent
2: Second Absorbent
3: First Low-Boiling-Point Material
4: First High-Boiling-Point Material
5: Second High-Boiling-Point Material
6: Second Low-Boiling-Point Material
7: Acetaldehyde
8: Third Low-Boiling-Point Material
9: First Incompressible Material

DETAILED DESCRIPTION

Hereinafter, the present specification will be described in more detail.

In the present specification, a description of a certain part "including" certain constituents means capable of further including other constituents, and does not exclude other constituents unless particularly stated on the contrary.

In the present specification, 'p to q' means a range of 'greater than or equal to p and less than or equal to q'.

Hereinafter, embodiments of the present disclosure will be described in detail with reference to accompanying drawings so that those having common knowledge in the art can readily implement the present disclosure. However, the present disclosure can be embodied in various different forms, and is not limited to the embodiments described herein.

One embodiment of the present application provides a process for producing acrylic acid, the process including a step 1 of separating a first low-boiling-point material including acetaldehyde (ACHO) and a first high-boiling-point material including acrylic acid (AA) by adding a first absorbent to a reaction product of a bio-raw material and cooling the result; a step 2 of separating a second low-boiling-point material including acetaldehyde (ACHO) and a second high-boiling-point material including acrylic acid (AA) by distilling the first high-boiling-point material including acrylic acid (AA); a step 3 of separating a first incompressible material and a third low-boiling-point material including acetaldehyde (ACHO) by adding a second absorbent to the first low-boiling-point material including acetaldehyde (ACHO) and cooling the result; and a step 4 of producing acrylic acid by purifying the second high-boiling-point material including acrylic acid (AA).

By the process for producing acrylic acid according to one embodiment of the present application including the step 1 of separating a first low-boiling-point material including acetaldehyde (ACHO) and a first high-boiling-point material including acrylic acid (AA) by adding a first absorbent to a reaction product of a bio-raw material and cooling the result and the step 2 of separating a second low-boiling-point material including acetaldehyde (ACHO) and a second high-boiling-point material including acrylic acid (AA), final acrylic acid can be produced in high purity and high yield.

Particularly, acetaldehyde is produced as a by-product in the reaction product of the bio-raw material since a dehydration reaction of lactic acid occurs at a high temperature (330° C. to 400° C.), and by the process for producing acrylic acid according to the disclosure of the present application including the step 3 in the process, acetaldehyde produced as a by-product can be commercialized as a high purity and high yield product while producing high purity and high yield acrylic acid as above, which enhances economic feasibility of the bioprocess since both acrylic acid and acetaldehyde can be obtained.

In other words, the present disclosure includes a process of producing bio-raw material-based acrylic acid instead of an existing petrochemical process of producing acrylic acid using an oxidation reaction of propylene, and the process for producing acrylic acid according to the present application is capable of obtaining high purity acrylic acid by including both the step 1 and the step 2 of separating a second low-boiling-point material including acetaldehyde (ACRO) and a second high-boiling-point material including acrylic acid (AA), and, by further including the step 3, is capable of obtaining high purity acetaldehyde as well, and accordingly, it is a main characteristic of the disclosure of the present application to enhance economic feasibility of the bioprocess by commercializing as well a material typically discarded as a by-product.

One embodiment of the present application provides the step 1 of separating a first low-boiling-point material including acetaldehyde (ACHO) and a first high-boiling-point material including acrylic acid (AA) by adding a first absorbent to a reaction product of a bio-raw material and cooling the result.

The reaction of the bio-raw material included in the step 1 can include a dehydration reaction of lactic acid, and can include any reaction without limit as long as it is a reaction of a bio-raw material for producing acrylic acid.

In one embodiment of the present application, the bio-raw material can be lactic acid in a gas phase.

In one embodiment of the present application, the gas phase can mean a vaporized state, that is, a state in which a liquid is vaporized to become a gas.

In the present application, the lactic acid is an organic compound having an asymmetric carbon atom to which four atomic groups of a carboxyl group, a hydroxyl group, a methyl group and hydrogen bond, and includes both D-lactic acid and L-lactic acid, and can mean a single lactic acid monomer.

In the present application, a lactic acid oligomer means a material obtained by lactic acid reacting to each other to form a dimer, a trimer and the like, and the lactic acid oligomer can mean a dimer to a 100-mer of lactic acid.

Lactic acid is a substance that polymerizes through an esterification reaction in a liquid phase without a catalyst even in the absence of water, and substances formed through a polymerization reaction of lactic acid can all be expressed as a lactic acid oligomer. In other words, all substances formed through a polymerization reaction of lactic acid other than a single lactic acid monomer can be defined as a lactic acid oligomer.

In the process for producing acrylic acid provided in one embodiment of the present application, the vapor phase lactic acid includes water and a lactic acid raw material, and the lactic acid raw material includes lactic acid and a lactic acid oligomer, and the lactic acid raw material is included in greater than or equal to 10 parts by weight and less than or equal to 100 parts by weight based on 100 parts by weight of the vapor phase lactic acid.

In another embodiment, the lactic acid raw material can be included in greater than or equal to 10 parts by weight and less than or equal to 100 parts by weight, preferably greater than or equal to 30 parts by weight and less than or equal to 100 parts by weight, and more preferably greater than or equal to 60 parts by weight and less than or equal to 100 parts by weight based on 100 parts by weight of the vapor phase lactic acid.

The vapor phase lactic acid is an aqueous lactic acid solution in a final vaporized state before producing acrylic acid, and by the lactic acid raw material content satisfying the above-mentioned range in the vapor phase lactic acid, the introduced amount of the lactic acid raw material itself is suitable, and the water content is adjusted to a proper range, and as a result, excellent economic feasibility is obtained in the process for producing acrylic acid according to the present application.

In the process for producing acrylic acid provided in one embodiment of the present application, a ratio of the lactic acid:lactic acid oligomer in the vapor phase lactic acid can be from 100:0 to 80:20.

In another embodiment, a ratio of the lactic acid:lactic acid oligomer in the vapor phase lactic acid can satisfy a range of 100:0 to 80:20, preferably 100:0 to 90:10 and more preferably 100:0 to 95:5.

In other words, the process for producing acrylic acid according to the present disclosure breaks from existing petrochemical-based manufacturing processes and produces acrylic acid based on lactic acid, an environmental-friendly bio-raw material, and as a result, excellent properties are obtained in terms of environmental protection while obtaining sustainability. The vapor phase lactic acid corresponds to the bio-raw material of the step 1 according to the present application, and fouling occurring in the reactor can be reduced for the process for producing final acrylic acid and the reaction yield can increase.

In one embodiment of the present application, the reaction product of the bio-raw material can include acrylic acid, acetaldehyde, carbon monoxide, carbon dioxide, water, hydrogen, a lactic acid monomer, acetic acid, 2,3-pentadione (2,3-PD) and propionic acid (PA).

Particularly, acetaldehyde is not produced in a petrochemical-based propylene oxidation reaction since the reaction temperature is from 250° C. to 270° C., however, acetaldehyde is produced as a by-product in the process for producing acrylic acid since a dehydration reaction of the vapor phase lactic acid in the reaction of the bio-raw material according to the present application occurs at a high temperature (330° C. to 400° C.), and commercializing acetaldehyde produced as a by-product herein is a main purpose of the present disclosure as well.

In the process for producing acrylic acid provided in one embodiment of the present application, the step 1 includes a step of separating through a cooling tower, and the cooling tower has a cooling temperature of higher than or equal to 10° C. and lower than or equal to 150° C. and an inner pressure of greater than or equal to 0.5 bar and less than or equal to 5.0 bar.

In another embodiment, the cooling tower can have an inner pressure of greater than or equal to 0.5 bar and less than or equal to 5.0 bar, preferably greater than or equal to 1.0 bar and less than or equal to 4.0 bar and more preferably greater than or equal to 2.0 bar and less than or equal to 3.5 bar, and can specifically satisfy an inner pressure of 3.0 bar.

In another embodiment, the cooling tower can have an inner temperature of 10° C. or higher, preferably 20° C. or higher and more preferably 40° C. or higher, and can be 200° C. or lower and preferably 150° C. or lower.

By the inner temperature and the inner pressure of the cooling tower satisfying the above-mentioned ranges in the step 1 as above, a content of acrylic acid included in the first low-boiling-point material discharged to an upper portion of the cooling tower can be minimized, that is, all acrylic acid in the reaction product of the bio-raw material is discharged to a lower portion of the cooling tower in the first high-boiling-point material including acrylic acid (AA), and as a result, yield and purity of the acrylic acid can increase.

In other words, in the process for producing acrylic acid, the step 1 can be a step of separating the first high-boiling-point material including acrylic acid from low-boiling point by-products through cooling.

In the process for producing acrylic acid provided in one embodiment of the present application, the first absorbent is included so that acrylic acid (AA) included in the first low-boiling-point material of the step 1 is included in 1 parts by weight or less with respect to 100 parts by weight of acrylic acid in the reaction product of the bio-raw material.

In the step 1 according to the present disclosure, acrylic acid in the reaction product of the bio-raw material can all be discharged to a lower portion of the cooling tower in the first high-boiling-point material including acrylic acid (AA) by adjusting, as well as adjusting the temperature and pressure ranges of the cooling tower as described above, the content of the first absorbent.

Specifically, in one embodiment of the present application, acrylic acid (AA) included in the first low-boiling-point material of the step 1 can be included in 1 parts by weight or less, preferably 0.5 parts by weight or less and more preferably 0.01 parts by weight or less, and can be 0 parts by weight or greater and preferably 0.005 parts by weight or greater with respect to 100 parts by weight of acrylic acid in the reaction product of the bio-raw material.

In other words, acrylic acid (AA) included in the first low-boiling-point material of the step 1 is an amount not obtained and discarded, and by adjusting the amount of the first absorbent as above, the weight of acrylic acid (AA) included in the first low-boiling-point material is adjusted as above, and an economically superior process for producing acrylic acid can be provided.

In the process for producing acrylic acid provided in one embodiment of the present application, when the cooling tower has a cooling temperature of higher than or equal to 10° C. and lower than or equal to 50° C., the first absorbent is included in greater than or equal to 1 parts by weight and less than or equal to 20 parts by weight with respect to 100 parts by weight of the reaction product of the bio-raw material of the step 1.

In another embodiment, the first absorbent can be included in greater than or equal to 1 parts by weight and less than or equal to 20 parts by weight, preferably greater than or equal to 2 parts by weight and less than or equal to 15 parts by weight, and more preferably greater than or equal to 3 parts by weight and less than or equal to 10 parts by weight with respect to 100 parts by weight of the reaction product of the bio-raw material of the step 1.

In the process for producing acrylic acid provided in one embodiment of the present application, when the cooling tower has a cooling temperature of higher than or equal to 50° C. and lower than or equal to 80° C., the first absorbent is included in greater than or equal to 35 parts by weight and less than or equal to 50 parts by weight with respect to 100 parts by weight of the reaction product of the bio-raw material of the step 1.

In another embodiment, the first absorbent can be included in greater than or equal to 35 parts by weight and less than or equal to 50 parts by weight, preferably greater than or equal to 37 parts by weight and less than or equal to 45 parts by weight, and more preferably greater than or equal to 40 parts by weight and less than or equal to 45 parts by weight with respect to 100 parts by weight of the reaction product of the bio-raw material of the step 1.

The process for producing acrylic acid of the present application adjusts the amount of heat of the cooling tower when conducting the step 1 as above and includes the first absorbent in the above-mentioned content range, and, by particularly including the first absorbent in the above-mentioned range, adjusts the first high-boiling-point material including acrylic acid, water and the like to be all discharged to a lower portion of the absorption tower, and accordingly, finally produced acrylic acid has increased yield and purity, and acetaldehyde produced as a by-product can also be produced in high purity.

FIG. 1 is a schematic diagram of the process for producing acrylic acid according to the present application, and specifically, it shows that the reaction product of the bio-raw material (A) is introduced to the cooling tower (B), and the boiling point-dependent separation process occurs by including the first absorbent (1), and it is identified herein that the first high-boiling-point material including acrylic acid (AA) (4) is separated to the lower portion, and the first low-boiling-point material including acetaldehyde (ACHO) (3) is separated to the upper portion.

In the process for producing acrylic acid provided in one embodiment of the present application, the first absorbent includes a material having a boiling point difference of 20° C. or higher compared to a normal boiling point (NBP) of the acrylic acid (AA) and a boiling point difference of 50° C. or higher compared to a normal boiling point (NBP) of the acetaldehyde (ACHO).

In the present application, the normal boiling point (NBP) is a synonym for a boiling point, and can mean a boiling point of a liquid when an external pressure is 1 atmosphere (760 mmHg). A boiling point of a material normally means a normal boiling point, and for example, a normal boiling point of water can be expressed as 100° C. It means a temperature at which not only evaporation occurs from a liquid surface, but also vaporization occurs from inside a liquid and bubbles start to generate, and can mean a temperature at which a change occurs in a material state from a liquid to a gas.

In another embodiment, the first absorbent can be a material having a boiling point difference of higher than or equal to 20° C. and lower than or equal to 40° C. compared to a normal boiling point (NBP) of the acrylic acid (AA) and a boiling point difference of higher than or equal to 50° C. and lower than or equal to 80° C. compared to a normal boiling point (NBP) of the acetaldehyde (ACHO).

In one embodiment of the present application, the acrylic acid has a normal boiling point of 141° C., and the acetaldehyde has a normal boiling point of 20° C.

In one embodiment of the present application, the first absorbent can be a material having a boiling point difference of higher than or equal to 20° C. and lower than or equal to 40° C. compared to a normal boiling point (NBP) of the acrylic acid (AA), having a boiling point difference of higher than or equal to 50° C. and lower than or equal to 80° C. compared to a normal boiling point (NBP) of the acetaldehyde (ACHO), and having a higher boiling point compared to the acetaldehyde.

In one embodiment of the present application, the first absorbent can be used without limit as long as the above-mentioned conditions are satisfied, and specifically, the first absorbent can include water in one embodiment of the present application.

In one embodiment of the present application, the first absorbent can satisfy a temperature range of higher than or equal to 10° C. and lower than or equal to 100° C.

In another embodiment, the first absorbent can satisfy a temperature range of higher than or equal to 10° C. and lower than or equal to 100° C., preferably higher than or equal to 20° C. and lower than or equal to 100° C., and most preferably higher than or equal to 30° C. and lower than or equal to 100° C.

By the first absorbent temperature range satisfying the above-mentioned range as above, the first absorbent temperature is adjusted to a similar range as the range of the inner temperature of the cooling tower when included in the cooling tower of the step 1, which enhances economic feasibility by reducing inner capacity of the cooling tower.

In one embodiment of the present application, the acrylic acid included in the first high-boiling-point material can be included in 95 parts by weight or greater based on 100 parts by weight of acrylic acid included in the reaction product of the bio-raw material.

In another embodiment, the acrylic acid included in the first high-boiling-point material can be included in 95 parts by weight or greater, preferably 97 parts by weight or greater and more preferably 99 parts by weight or greater, and can be 100 parts by weight or less based on 100 parts by weight of acrylic acid included in the reaction product of the bio-raw material.

In one embodiment of the present application, the acetaldehyde included in the first low-boiling-point material can be included in 90 parts by weight or greater based on 100 parts by weight of acetaldehyde included in the reaction product of the bio-raw material.

In another embodiment, the acetaldehyde included in the first low-boiling-point material can be included in 90 parts by weight or greater, preferably 93 parts by weight or greater and more preferably 95 parts by weight or greater, and can be 100 parts by weight based on 100 parts by weight of acetaldehyde included in the reaction product of the bio-raw material.

One embodiment of the present application provides the step 2 of separating a second low-boiling-point material including acetaldehyde (ACHO) and a second high-boiling-point material including acrylic acid (AA) by distilling the first high-boiling-point material including acrylic acid (AA).

In one embodiment of the present application, the step 2 is a step of once more distilling the first high-boiling-point material including acrylic acid (AA) discharged to a lower portion of the cooling tower in the step 1, and corresponds to a step of separating a second low-boiling-point material including acetaldehyde (ACHO) and a second high-boiling-point material including acrylic acid (AA).

In other words, through such a process of the step 2, acetaldehyde that can be discharged to a lower portion of the cooling tower in the step 1 can be further separated to obtain high yield and high purity acrylic acid, and by obtaining a second low-boiling-point material including acetaldehyde (ACHO), high yield and high purity acetaldehyde can be obtained through a separation process of the step 3 to be described later.

In one embodiment of the present application, the first high-boiling-point material including acrylic acid (AA) can include water, acrylic acid, and acetaldehyde.

In one embodiment of the present application, acrylic acid included in the second high-boiling-point material can be included in 95 parts by weight or greater based on 100 parts by weight of the acrylic acid included in the first high-boiling-point material including acrylic acid (AA).

In another embodiment, acrylic acid included in the second high-boiling-point material can be included in 95 parts by weight or greater, preferably 97 parts by weight or greater and more preferably 99 parts by weight or greater, and can be 100 parts by weight or less and preferably 99.99 parts by weight or less based on the 100 parts by weight of the acrylic acid included in the first high-boiling-point material including acrylic acid (AA).

In the process for producing acrylic acid according to the present disclosure, the yield of finally produced acrylic acid included in the second high-boiling-point material can be high by going through the process of adding the absorbent and cooling in the step 1 and separating acetaldehyde once again in the step 2.

In one embodiment of the present application, the second high-boiling-point material can be purified to obtain final acrylic acid.

In one embodiment of the present application, the acetaldehyde included in the second low-boiling-point material can be included in 95 parts by weight or greater based on 100 parts by weight of the acetaldehyde included in the first high-boiling-point material including acrylic acid (AA).

In another embodiment, the acetaldehyde included in the second low-boiling-point material can be included in 95 parts by weight or greater, preferably 96 parts by weight or greater and more preferably 97 parts by weight or greater, and can be 100 parts by weight or less and preferably 99.99 parts by weight or less based on 100 parts by weight of the acetaldehyde included in the first high-boiling-point material including acrylic acid (AA).

As described above, while obtaining acrylic acid in a high yield, acetaldehyde can be also commercialized by separating the acetaldehyde included in the first high-boiling-point material including acrylic acid (AA) again and going through a process to be described later.

FIG. 1 is a schematic diagram of the process for producing acrylic acid according to the present application, and it can be seen that the step 2 specifically separates the first high-boiling-point material including acrylic acid (AA) (4) through a distillation tower (E) to obtain the second high-boiling-point material including acrylic acid (AA) (5), and supplies the second low-boiling-point material including acetaldehyde (ACHO) (6) to a process to be described later.

One embodiment of the present application provides the step 3 of separating a first incompressible material and a third low-boiling-point material including acetaldehyde (ACHO) by adding a second absorbent to the first low-boiling-point material including acetaldehyde (ACHO) and cooling the result.

In the process for producing acrylic acid of the present application, the step 3 is a process of adding a second absorbent to the first low-boiling-point material discharged to an upper portion of the cooling tower in the step 1 and cooling the result, and through such a process, acetaldehyde produced as a by-product in the process for producing acrylic acid can also be commercialized. In other words, it is a step of commercializing high purity acetaldehyde as well while obtaining high purity acrylic acid, which is considered as a characteristic of the disclosure of the present application, and can be a main characteristic of the present disclosure.

In the process for producing acrylic acid provided in one embodiment of the present application, the step 3 includes a step of separating through an absorption tower, and the absorption tower has a temperature of is higher than or equal to 0° C. and lower than or equal to 100° C. and an inner pressure of greater than or equal to 0.1 bar and less than or equal to 10.0 bar.

In another embodiment, the absorption tower of the step 3 can have an inner pressure of greater than or equal to 0.1 bar and less than or equal to 10.0 bar, preferably greater than or equal to 1.0 bar and less than or equal to 8.0 bar and more preferably greater than or equal to 1.5 bar and less than or equal to 5.0 bar, and can specifically satisfy an inner pressure of 2.5 bar.

In another embodiment, the absorption tower of the step 3 can have an inner temperature of 0° C. or higher, preferably 5° C. or higher and more preferably 10° C. or higher, and can be 100° C. or lower and preferably 80° C. or lower.

By the inner temperature and the inner pressure of the absorption tower satisfying the above-mentioned ranges in the step 3 as above, the acetaldehyde included in the first low-boiling-point material discharged to an upper portion of the absorption tower can be commercialized in high yield and high purity, and by the process of separating from the first incompressible material included in the first low-boiling-point material progressing smoothly in particular, acetaldehyde can be obtained in high yield and high purity while obtaining acrylic acid.

In the process for producing acrylic acid provided in one embodiment of the present application, the second absorbent is included so that acetaldehyde (ACHO) included in the first incompressible material of the step 3 is included in 1 parts by weight or less with respect to 100 parts by weight of acetaldehyde in the reaction product of the bio-raw material.

In the step 3 according to the present disclosure, acetaldehyde in the reaction product of the bio-raw material can all be discharged to a lower portion of the absorption tower in the first low-boiling-point material including acetaldehyde (ACHO) by adjusting the content of the second absorbent.

Specifically, in one embodiment of the present application, acetaldehyde (ACHO) included in the first incompressible material of the step 3 can be included in 2 parts by weight or less, preferably 1.0 parts by weight or less and more preferably 0.5 parts by weight or less, and can be 0 parts by weight or greater and preferably 0.005 parts by weight or greater with respect to 100 parts by weight of acetaldehyde in the reaction product of the bio-raw material.

In other words, another characteristic of the process for producing acrylic acid according to the present application is commercializing acetaldehyde produced as a by-product, and by adjusting the amount of the second absorbent as above, loss of the acetaldehyde can be minimized.

The process for producing acrylic acid of the present application includes the second absorbent in the above-mentioned content range when conducting the step 3 as above, and, by particularly including the second absorbent in the above-mentioned range, adjusts only the third low-boiling-point material including acetaldehyde to be discharged to a lower portion of the absorption tower of the step 3 in the first low-boiling-point material including acetaldehyde, an incompressible material and the like, and finally produced acetaldehyde has increased yield and purity.

In the process for producing acrylic acid provided in one embodiment of the present application, the second absorbent includes, as a material having a higher boiling point compared to a normal boiling point (NBP) of the acetaldehyde (ACHO), a material having a boiling point difference of 20° C. or higher.

In the process for producing acrylic acid provided in another embodiment, the second absorbent includes, as a material having a higher boiling point compared to a normal boiling point (NBP) of the acetaldehyde (ACHO), a material having a boiling point difference of higher than or equal to 20° C. and lower than or equal to 100° C.

In the process for producing acrylic acid provided in another embodiment, the second absorbent includes, as a material having a higher boiling point compared to a normal boiling point (NBP) of the acetaldehyde (ACHO), a material having a boiling point difference of higher than or equal to 20° C. and lower than or equal to 100° C., preferably having a boiling point difference of higher than or equal to 30° C. and lower than or equal to 90° C., and more preferably having a boiling point difference of higher than or equal to 50° C. and lower than or equal to 80° C.

In another embodiment, the second absorbent can be a material having a higher boiling point compared to a boiling point of the acetaldehyde.

In one embodiment of the present application, the second absorbent can include one or more selected from the group consisting of water and acrylic acid.

In one embodiment of the present application, the second absorbent can satisfy a temperature range of higher than or equal to −5° C. and lower than or equal to 20° C.

In another embodiment, the second absorbent can satisfy a temperature range of higher than or equal to −5° C. and lower than or equal to 20° C., preferably higher than or equal to 5° C. and lower than or equal to 15° C., and most preferably higher than or equal to 5° C. and lower than or equal to 10° C.

By the second absorbent temperature range satisfying the above-mentioned range as above, the second absorbent temperature is adjusted to a similar range as the range of the inner temperature of the absorption tower when included in the absorption tower of the step 3, which enhances economic feasibility by reducing inner capacity of the absorption tower.

In one embodiment of the present application, the acetaldehyde included in the third low-boiling-point material can be included in 95 parts by weight or greater based on 100 parts by weight of the acetaldehyde included in the first low-boiling-point material.

In another embodiment, the acetaldehyde included in the third low-boiling-point material can be included in 95 parts by weight or greater, preferably 96 parts by weight or greater and more preferably 97 parts by weight or greater, and can be 100 parts by weight or less and preferably 99.9 parts by weight or less based on 100 parts by weight of the acetaldehyde included in the first low-boiling-point material.

In one embodiment of the present application, the first incompressible material can include carbon monoxide, carbon dioxide and an inert gas.

The step 3 of the present application can be seen in FIG. 1, and specifically, the process of supplying the first low-boiling-point material (3) to the absorption tower (C), and then supplying the second absorbent (2) to separate the first incompressible material (9) including an inert gas and the third low-boiling-point material (8) can be seen.

In the process for producing acrylic acid provided in one embodiment of the present application, a step of separating the second low-boiling-point material including acetaldehyde (ACHO) and the third low-boiling-point material including acetaldehyde (ACHO) to separate acetaldehyde and the second absorbent is further included.

In the process for producing acrylic acid provided in one embodiment of the present application, the step includes a step of separating through a separation tower, and the separation tower has a temperature of higher than or equal to 10° C. and lower than or equal to 200° C. and an inner pressure of greater than or equal to 0.3 bar and less than or equal to 10.0 bar.

In one embodiment of the present application the step can be expressed as step 3-1.

In other words, the process of the step 3-1 corresponds to a process of separating the second absorbent and obtaining pure acetaldehyde for acetaldehyde commercialization.

In another embodiment, the separation tower of the step has an inner pressure of greater than or equal to 0.3 bar and less than or equal to 10.0 bar, preferably greater than or equal to 1.0 bar and less than or equal to 8.0 bar and more preferably greater than or equal to 2.0 bar and less than or equal to 5.0 bar, and can specifically satisfy an inner pressure of 3.0 bar.

In another embodiment, the separation tower of the step has an inner temperature of 10° C. or higher, preferably 20° C. or higher and more preferably 40° C. or higher, and can be 200° C. or lower and preferably 150° C. or lower.

By the inner temperature and the inner pressure of the separation tower satisfying the above-mentioned ranges as above, the acetaldehyde included in the third low-boiling-point material discharged to a lower portion of the absorption tower of the step 3 can be commercialized in high yield and high purity, and by the process of separating from the second absorbent included in the third low-boiling-point material progressing smoothly in particular, acetaldehyde can be obtained in high yield and high purity while obtaining acrylic acid.

In other words, final acetaldehyde is obtained by combining the second low-boiling-point material including acetaldehyde (ACHO) discharged to an upper portion of the distillation tower in the step 2 and the third low-boiling-point material discharged to a lower portion of the absorption tower through the step 3, and the process for producing acrylic acid according to one embodiment of the present application minimizes loss of acrylic acid and acetaldehyde during the process.

In addition, after separating acetaldehyde and the second absorbent as above, the second absorbent can be included again in the step 3 through a liquid flow, and the amount of the second absorbent used can also be minimized.

In one embodiment of the present application, a step of cooling the second absorbent using a refrigerant can be further included after separating acetaldehyde and the second absorbent.

In other words, in the process for producing acrylic acid provided in one embodiment of the present application, the second absorbent included in the step 3 can include the second absorbent supplied from the outside and the second absorbent reused through the liquid flow as above, and by including the step of cooling with a refrigerant, the second absorbent has a temperature of higher than or equal to −5° C. and lower than or equal to 20° C.

By the second absorbent temperature satisfying the above-mentioned range as above, an adjustment can be made to absorb 99 wt % or greater of the acetaldehyde in the first low-boiling-point material including acetaldehyde (ACHO).

In the process for producing acrylic acid provided in one embodiment of the present application, purity of the acetaldehyde is 95% or greater, and the recovery rate based on the reaction product of the bio-raw material is 95% or greater.

In another embodiment, purity of the acetaldehyde can be 100% or less, and 99.99% or less.

In other words, the process for producing acrylic acid according to the disclosure of the present application is capable of producing final acrylic acid in high purity and high yield by including the step 1 of separating a first low-boiling-point material including acetaldehyde (ACHO) and a first high-boiling-point material including acrylic acid (AA) by adding a first absorbent to a reaction product of a bio-raw material and cooling the result and the step 2 of separating a second low-boiling-point material including acetaldehyde (ACHO) and a second high-boiling-point material including acrylic acid (AA), and in addition thereto, is capable of commercializing acetaldehyde, which is produced as a by-product, as a high purity and high yield product as well by including the step 3 and the separation process through the separation tower in the process, and as a result, acrylic acid and acetaldehyde can all be obtained, which enhances economic feasibility of the bioprocess.

The production process of the present disclosure is particularly useful for synthesizing acrylic acid, and specifically, the vapor composition including lactic acid obtained in the present disclosure can be brought into contact with a dehydration catalyst to prepare acrylic acid. A produced reaction gas is collected and liquefied by cooling or bringing into contact with a collection liquid, and after going through a purification process such as extraction, distillation and crystallization, high purity acrylic acid can be obtained. Produced acrylic acid is widely used as a raw material of absorbent polymers, paints, adhesives or the like.

Hereinafter, examples of the present disclosure will be described in detail so that those having common knowledge in the art can readily implement the present disclosure. However, the present disclosure can be embodied in various different forms, and is not limited to the examples described herein.

PREPARATION EXAMPLE

The following examples and comparative examples were simulated by Aspen Plus of Aspen Technology Inc.

Example 1

An operation process of Example 1 is shown in FIG. 1, and as illustrated in FIG. 1, a flow rate included in each step and a weight ratio (wt %) of main components that can be included in the flow rate are as shown in the following Table 1 to Table 4.

TABLE 1

| Step 1 | | A | 1 | 3 | 4 |
|---|---|---|---|---|---|
| Flow Rate (kg/hr) | | 14880 | 500 | 2233 | 13148 |
| Temperature (° C.) | | 150 | 40.0 | 94.6 | 129.5 |
| Composition (wt %) | Water | 50.4 | 500 kg/hr (100 wt %) | 16.5 | 58.1 |
| | Acrylic Acid | 33.6 | — | 0.1 | 38.0 |
| | Acetaldehyde | 6.7 | — | 42.9 | 0.4 |
| | Inert Gas (CO, $CO_2$, $H_2$) | 6.1 | — | 40.5 | — |
| | High-Boiling-Point Material (2,3-PD, PA) | 3.1 | — | — | 3.5 |

In the step 1, the cooling tower was operated at a cooling temperature of approximately 95° C. to 130° C. and an inner pressure of 3.0 bar. In addition, the first absorbent included in the step 1 had a normal boiling point of 100° C.

TABLE 2

| Step 2 | | 4 | 5 | 6 |
|---|---|---|---|---|
| Flow Rate (kg/hr) | | 13148 | 13048 | 100 |
| Temperature (° C.) | | 129.5 | 128.1 | 40.0 |
| Composition (wt %) | Water | 58.1 | 58.2 | 46.0 |
| | Acrylic Acid | 38.0 | 38.3 | 4.3 |
| | Acetaldehyde | 0.4 | — | 47.0 |
| | Inert Gas (CO, $CO_2$, $H_2$) | — | — | — |
| | High-Boiling-Point Material (2,3-PD, PA) | 3.5 | 3.5 | 3.0 |

In the step 2, the distillation tower was operated at a temperature of approximately 40° C. to 130° C. and an inner pressure of 2.5 bar.

TABLE 3

| Step 3 | | 3 | 2 | 8 | 9 |
|---|---|---|---|---|---|
| Flow Rate (kg/hr) | | 2233 | 7480 | 8797 | 916 |
| Temperature (° C.) | | 94.6 | 5 | 61.2 | 12.0 |
| Composition (wt %) | Water | 16.5 | 97.7 | 87.2 | 0.3 |
| | Acrylic Acid | 0.1 | 1.4 | 1.2 | — |
| | Acetaldehyde | 42.9 | — | 10.7 | 1.3 |
| | Inert Gas (CO, $CO_2$, $H_2$) | 40.5 | — | — | 98.4 |
| | High-Boiling-Point Material (2,3-PD, PA) | — | — | — | — |

In the step 3, the absorption tower was operated at a temperature of approximately 12° C. to 61° C. and an inner pressure of 2.5 bar. In addition, the second absorbent included in the step 3 had a normal boiling point of 100° C.

TABLE 4

| Step 3-1 | | 6 | 8 | 2 | 7 |
|---|---|---|---|---|---|
| Flow Rate (kg/hr) | | 100 | 8797 | 7480 | 1017 |
| Temperature (° C.) | | 40 | 61.2 | 5 | 40 |
| Composition (wt %) | Water | 46.0 | 87.2 | 97.7 | 3.1 |
| | Acrylic Acid | 4.3 | 1.2 | 1.4 | 0.0 |
| | Acetaldehyde | 47.0 | 10.7 | — | 96.9 |
| | Inert Gas (CO, $CO_2$, $H_2$) | — | — | — | — |
| | High-Boiling-Point Material (2,3-PD, PA) | 3.0 | — | — | — |

In the step 3-1, the separation tower was operated at a temperature of approximately 40° C. to 133° C. and an inner pressure of 3.0 bar.

Example 2

An operation process of Example 2 is shown in FIG. 1, and as illustrated in FIG. 1, a flow rate included in each step and a weight ratio (wt %) of main components that can be included in the flow rate are as shown in the following Table 5 to Table 8.

Particularly, unlike Example 1, the cooling calorie (amount of cooling heat used for cooling) of the cooling tower was reduced, and the amount of the first absorbent used increased in Example 2, and it corresponds to a process of resultantly increasing the content of water discharged to an upper portion of the cooling tower and thereby increasing the used amount of the second absorbent used in the absorption tower.

TABLE 5

| Step 1 | | A | 1 | 3 | 4 |
|---|---|---|---|---|---|
| Flow Rate (kg/hr) | | 14880 | 6000 | 2741 | 18140 |
| Temperature (° C.) | | 150 | 40 | 110 | 129 |
| Composition | Water | 50.4 | 6000 kg/hr | 32.2 | 69.6 |
| (wt %) | | | (100 wt %) | | |
| | Acrylic Acid | 33.6 | — | 0.1 | 27.6 |
| | Acetaldehyde | 6.7 | — | 34.7 | 0.3 |
| | Inert Gas (CO, $CO_2$, $H_2$) | 6.1 | — | 33.0 | — |
| | High-Boiling-Point Material (2,3-PD, PA) | 3.1 | — | — | 2.6 |

In the step 1, the cooling tower was operated at a cooling temperature of approximately 110° C. to 130° C. and an inner pressure of 3.0 bar.

TABLE 6

| Step 2 | | 4 | 5 | 6 |
|---|---|---|---|---|
| Flow Rate (kg/hr) | | 18140 | 18040 | 100 |
| Temperature (° C.) | | 129 | 127.7 | 40.0 |
| Composition | Water | 69.6 | 69.7 | 46.0 |
| (wt %) | Acrylic Acid | 27.6 | 27.7 | 4.3 |
| | Acetaldehyde | 0.3 | 0.0 | 47.0 |
| | Inert Gas (CO, $CO_2$, $H_2$) | — | — | — |
| | High-Boiling-Point Material (2,3-PD, PA) | 2.6 | 2.6 | 2.0 |

In the step 2, the distillation tower was operated at a temperature of approximately 40° C. to 128° C. and an inner pressure of 2.5 bar.

TABLE 7

| Step 3 | | 3 | 2 | 8 | 9 |
|---|---|---|---|---|---|
| Flow Rate (kg/hr) | | 2741 | 10540 | 12369 | 912 |
| Temperature (° C.) | | 110 | 5 | 72.1 | 10.5 |
| Composition | Water | 32.2 | 99.0 | 91.5 | 0.3 |
| (wt %) | Acrylic Acid | 0.1 | 0.6 | 0.6 | — |
| | Acetaldehyde | 34.7 | — | 7.6 | 1.0 |
| | Inert Gas (CO, $CO_2$, $H_2$) | 33.0 | — | 0.04 | 98.7 |
| | High-Boiling-Point Material (2,3-PD, PA) | — | 0.4 | 0.3 | — |

In the step 3, the absorption tower was operated at a temperature of approximately 11° C. to 72° C. and an inner pressure of 2.5 bar.

TABLE 8

| Step 3-1 | | 6 | 8 | 2 | 7 |
|---|---|---|---|---|---|
| Flow Rate (kg/hr) | | 100 | 12369 | 10540 | 1028 |
| Temperature (° C.) | | 40.0 | 72.1 | 5 | 40.0 |
| Composition | Water | 46.0 | 91.5 | 99.0 | 3.7 |
| (wt %) | Acrylic Acid | 4.3 | 0.6 | 0.6 | 0.0 |
| | Acetaldehyde | 47.0 | 7.6 | — | 96.2 |
| | Inert Gas (CO, $CO_2$, $H_2$) | — | — | — | — |
| | High-Boiling-Point Material (2,3-PD, PA) | 2.0 | 0.3 | 0.4 | — |

In the step 3-1, the separation tower was operated at a temperature of approximately 40° C. to 133° C. and an inner pressure of 3.0 bar.

Example 3

An operation process of Example 3 identified shown in FIG. 1, and as illustrated in FIG. 1, a flow rate included in each step and a weight ratio (wt %) of main components that can be included in the flow rate are as shown in the following Table 9 to Table 12.

TABLE 9

| Step 1 | | A | 1 | 3 | 4 |
|---|---|---|---|---|---|
| Flow Rate (kg/hr) | | 11787.9 | 1000 | 3109.2 | 9678.7 |
| Temperature (° C.) | | 150 | 40 | 92.3 | 121.2 |
| Composition | Water | 53.8 | 1000 kr/hr | 20.4 | 69.3 |
| (wt %) | | | (100 wt %) | | |
| | Acrylic Acid | 24.1 | — | 0.1 | 29.4 |
| | Acetaldehyde | 7.3 | — | 26.8 | 0.2 |
| | Inert Gas (CO, $CO_2$, $H_2$) | 6.7 | — | 25.3 | — |
| | High-Boiling-Point Material (2,3-PD, PA) | 0.9 | — | — | 1.1 |
| | Carrier Gas ($N_2$) | 7.2 | — | 27.3 | — |

In the step 1, the cooling tower was operated at a cooling temperature of approximately 92° C. to 121° C. and an inner pressure of 2.5 bar.

TABLE 10

| Step 2 | | 4 | 5 | 6 |
|---|---|---|---|---|
| Flow Rate (kg/hr) | | 9678.7 | 9578.7 | 98.1 |
| Temperature (° C.) | | 121.2 | 120.8 | 55.5 |
| Composition | Water | 69.3 | 69.3 | 70.8 |
| (wt %) | Acrylic Acid | 39.4 | 29.6 | 6.8 |
| | Acetaldehyde | 0.2 | — | 21.2 |
| | Inert Gas (CO, $CO_2$, $H_2$) | — | — | — |
| | High-Boiling-Point Material (2,3-PD, PA) | 1.1 | 1.1 | 1.0 |
| | Carrier Gas ($N_2$) | — | — | — |

In the step 2, the distillation tower was operated at a temperature of approximately 56° C. to 121° C. an inner pressure of 2.5 bar.

TABLE 11

| Step 3 | | 3 | 2 | 8 | 9 |
|---|---|---|---|---|---|
| Flow Rate (kg/hr) | | 3109.2 | 10850.0 | 12310.8 | 1648.5 |
| Temperature (° C.) | | 92.3 | 5 | 58.1 | 7.5 |
| Composition | Water | 20.4 | 98.6 | 92.0 | 0.4 |
| (wt %) | Acrylic Acid | 0.1 | 1.2 | 1.1 | — |
| | Acetaldehyde | 26.8 | — | 6.7 | 0.4 |
| | Inert Gas (CO, CO₂, H₂) | 25.3 | — | — | 47.6 |
| | High-Boiling-Point Material (2,3-PD, PA) | — | 0.2 | 0.2 | — |
| | Carrier Gas (N₂) | 27.3 | — | — | 51.6 |

In the step 3, the absorption tower was operated at a temperature of approximately 8° C. to 58° C. and an inner pressure of 2.0 bar.

TABLE 12

| Step 3-1 | | 6 | 8 | 2 | 7 |
|---|---|---|---|---|---|
| Flow Rate (kg/hr) | | 98.1 | 12310.8 | 10850.0 | 887.3 |
| Temperature (° C.) | | 55.5 | 58.1 | 5 | 40.0 |
| Composition | Water | 70.8 | 92.0 | 98.6 | 4.9 |
| (wt %) | Acrylic Acid | 6.5 | 1.1 | 1.2 | — |
| | Acetaldehyde | 21.2 | 6.7 | — | 95.0 |
| | Inert Gas (CO, CO₂, H₂) | — | — | — | 0.1 |
| | High-Boiling-Point Material (2,3-PD, PA) | — | 0.2 | 0.2 | — |
| | Carrier Gas (N₂) | — | — | — | — |

In the step 3-1, the separation tower was operated at a temperature of approximately 40° C. to 133° C. and an inner pressure of 3.0 bar.

Comparative Example 1

A process of Comparative Example 1 was conducted in the same manner as in Example 1 except that the second absorbent was not included when compared with the production process of Example 1. Specifically, as seen from FIG. 2, the recovery rate of ACHO not including the second absorbent was 12.7 wt %, and it was identified that commercialization of ACHO was difficult. In addition thereto, it was identified that, in order to obtain ACHO at the level of Example 1 without using the second absorbent, the ACHO recovery rate of approximately 98.1 wt % was satisfied when conducting a cooling process three times (C-1, C-2, C-3), and a system capable of cooling to approximately −45° C. was required.

Specific information on the flow rate and the composition is as shown in the following Table 13.

TABLE 13

| Step 3 | | 3 | 8 | 9 |
|---|---|---|---|---|
| Flow Rate (kg/hr) | | 2233 | 474 | 1760 |
| Temperature (° C.) | | 94.6 | 37 | −45 |
| Composition | Water | 16.5 | 73.4 | 1.2 |
| (wt %) | Acrylic Acid | 0.1 | 0.3 | — |
| | Acetaldehyde | 42.9 | 25.7 | 47.4 |
| | Inert Gas (CO, CO₂, H₂) | 40.5 | 0.6 | 51.3 |

TABLE 13-continued

| Step 3 | | 3 | 8 | 9 |
|---|---|---|---|---|
| | High-Boiling-Point Material (2,3-PD, PA) | — | — | — |

Information on the flow rates (kg/hr) of acetic acid and acetaldehyde respectively included in the second high-boiling-point material (5) and the acetaldehyde (7) with respect to the initially introduced reaction product of the bio-raw material (A) according to Examples 1 to 3 and Comparative Example 1 is as shown in the following Table 14.

TABLE 14

| | | Acetic Acid | Acetaldehyde |
|---|---|---|---|
| Initially Introduced | Example 1 | 5000 | 1004 |
| Reaction Product of | Example 2 | 5000 | 1004 |
| Bio-Raw Material (A) | Example 3 | 2843.8 | 855.8 |
| | Comparative Example 1 | 5000 | 1004 |
| Second High-Boiling- | Example 1 | 4994.2 | 0 |
| Point Material (5) | Example 2 | 4994.4 | 0 |
| | Example 3 | 2835.4 | 0 |
| | Comparative Example 1 | 4994.2 | 0 |
| Acetaldehyde (7) | Example 1 | 0.2 | 985 |
| | Example 2 | 0.1 | 989 |
| | Example 3 | 0.3 | 843 |
| | Comparative Example 1 | 1.4 | 122 |

As seen from Examples 1 to 3 of Table 14, the process for producing acrylic acid according to one embodiment of the present application includes the step 1 of separating a first low-boiling-point material including acetaldehyde (ACHO) and a first high-boiling-point material including acrylic acid (AA) by adding a first absorbent to a reaction product of a bio-raw material and cooling the result and the step 2 of separating a second low-boiling-point material including acetaldehyde (ACHO) and a second high-boiling-point material including acrylic acid (AA), and accordingly, final acrylic acid can be produced in high purity and high yield.

Particularly, acetaldehyde is produced as a by-product in the reaction product of the bio-raw material since a dehydration reaction of lactic acid occurs at a high temperature (330° C. to 400° C.), and by the process for producing acrylic acid according to the disclosure of the present application including the step 3 in the process (second absorbent), acetaldehyde produced as a by-product can also be commercialized as a high purity and high yield product while producing high purity and high yield acrylic acid as above, and it was identified that economic feasibility of the bioprocess was enhanced since both acrylic acid and acetaldehyde were obtained.

As seen from Comparative Example 1 of Table 14, Comparative Example 1 is a case in which the second absorbent was not used, and although acetic acid was efficiently obtained, the amount of acetaldehyde recovered was 122 kg/hr, which was only 12.7 wt % recovered compared to the initial raw material, and it was identified that acetaldehyde produced as a by-product was not able to be commercialized, and it was also seen that, when the second absorbent was not used, acetaldehyde was recovered enough to be commercialized when additionally going through a cooling process three times as in FIG. 3. In other words, it was identified that additional process and costs are required when not using the second absorbent since a cooling process needs to be added three or more times for commercialization of the acetaldehyde.

The invention claimed is:

1. A process for producing acrylic acid, the process comprising:

(step 1) separating a first low-boiling-point material including acetaldehyde (ACHO) and a first high-boiling-point material including acrylic acid (AA) by adding a first absorbent to a reaction product of a bio-raw material and cooling the result;

(step 2) separating a second low-boiling-point material including acetaldehyde (ACHO) and a second high-boiling-point material including acrylic acid (AA) by distilling the first high-boiling-point material including acrylic acid (AA);

(step 3) separating a first incompressible material and a third low-boiling-point material including acetaldehyde (ACHO) by adding a second absorbent to the first low-boiling-point material including acetaldehyde (ACHO) and cooling the result; and (step 4) producing acrylic acid by purifying the second high-boiling-point material including acrylic acid (AA), wherein the step 3 includes a step of separating through an absorption tower; and the absorption tower has a temperature of higher than or equal to 0° C. and lower than or equal to 100° C. and an inner pressure of greater than or equal to 0.1 bar and less than or equal to 10.0 bar.

2. The process of claim 1, wherein the first absorbent includes a material having a boiling point difference of 20° C. or higher compared to a normal boiling point (NBP) of the acrylic acid (AA) and a boiling point difference of 50° C. or higher compared to a normal boiling point (NBP) of the acetaldehyde (ACHO).

3. The process of claim 1, wherein the second absorbent includes, as a material having a higher boiling point compared to a normal boiling point (NBP) of the acetaldehyde (ACHO), a material having a boiling point difference of 20° C. or higher.

4. The process of claim 1, wherein the step 1 includes a step of separating through a cooling tower; and the cooling tower has a cooling temperature of higher than or equal to 10° C. and lower than or equal to 150° C. and an inner pressure of greater than or equal to 0.5 bar and less than or equal to 5.0 bar.

5. The process of claim 1, wherein the first absorbent is included so that acrylic acid (AA) included in the first low-boiling-point material of the step 1 is included in 1 parts by weight or less with respect to 100 parts by weight of acrylic acid in the reaction product of the bio-raw material.

6. The process of claim 1, wherein the second absorbent is included so that acetaldehyde (ACHO) included in the first incompressible material of the step 3 is included in 1 parts by weight or less with respect to 100 parts by weight of acetaldehyde in the reaction product of the bio-raw material.

7. The process of claim 1, wherein separating of the second low-boiling-point material including acetaldehyde (ACHO) is carried out in step 2 and the separating of the third low-boiling-point material including acetaldehyde (ACHO) is carried out in step 3 to separate acetaldehyde and the second absorbent.

8. The process of claim 7, wherein the separating the second low-boiling-point material includes separating through a separation tower; and the separation tower has a temperature of higher than or equal to 10° C. and lower than or equal to 200° C. and an inner pressure of greater than or equal to 0.3 bar and less than or equal to 10.0 bar.

9. The process of claim 1, wherein the second absorbent has a temperature of higher than or equal to −5° C. and lower than or equal to 20° C.

10. The process of claim 7, wherein a purity of the acetaldehyde is 95% or greater, and a recovery rate thereof based on the reaction product of the bio-raw material is 95% or greater.

* * * * *